(12) United States Patent
Pagoria et al.

(10) Patent No.: US 8,071,813 B2
(45) Date of Patent: Dec. 6, 2011

(54) METHODS OF USING IONIC LIQUIDS HAVING A FLUORIDE ANION AS SOLVENTS

(75) Inventors: Philip Pagoria, Livermore, CA (US); Amitesh Maiti, San Ramon, CA (US); Alexander Gash, Brentwood, CA (US); Thomas Yong Han, Pleasanton, CA (US); Christine Orme, Oakland, CA (US); Laurence Fried, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 10 days.

(21) Appl. No.: 12/108,347

(22) Filed: Apr. 23, 2008

(65) Prior Publication Data

US 2009/0012297 A1    Jan. 8, 2009

Related U.S. Application Data

(60) Provisional application No. 60/927,845, filed on May 3, 2007.

(51) Int. Cl.
*C07C 209/00*    (2006.01)

(52) U.S. Cl. ..................... 564/437; 548/335.1
(58) Field of Classification Search ............... 548/335.1; 564/437
See application file for complete search history.

(56) References Cited

OTHER PUBLICATIONS

"No References Cited".*

* cited by examiner

*Primary Examiner* — James O Wilson
*Assistant Examiner* — Douglas M Willis

(57) ABSTRACT

A method in one embodiment includes contacting a strongly hydrogen bonded organic material with an ionic liquid having a fluoride anion for solubilizing the strongly hydrogen bonded organic material; and maintaining the ionic liquid at a temperature of about 90° C. or less during the contacting. A method in another embodiment includes contacting a strongly hydrogen bonded organic material with an ionic liquid having an acetate or formate anion for solubilizing the strongly hydrogen bonded organic material; and maintaining the ionic liquid at a temperature of less than about 90° C. during the contacting.

7 Claims, 2 Drawing Sheets

R= -CH$_2$-, O

R'= alkyl, alkoxyalky, R"= alkyl or alkoxyalkyl different than R'

X$^-$ = OAc, OCOH, F, OCOOR''', OR''',

R'''= alkyl

Y= S, O

METHODS OF USING IONIC LIQUIDS HAVING A FLUORIDE ANION AS SOLVENTS

RELATED APPLICATIONS

This application claims priority to provisional U.S. application Ser. No. 60/927,845 filed on May 3, 2007, which is herein incorporated by reference.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to solvents, and more particularly to ionic liquids as solvents for strongly hydrogen bonded materials.

BACKGROUND 1,3,5-triamino-2,4,6-trinitrobenzene (TATB) and 2,6-diamino-3,5-dinitropyrazine-1-oxide (LLM-105) are thermally stable, insensitive molecules with crystal densities of 1.938 and 1.918 g/cc, respectively. These insensitive molecules are strongly hydrogen-bonded molecules that are generally insoluble in most conventional organic solvents but show some solubility in polar, aprotic solvents, such as DMSO, at high-temperatures. However, the high temperatures necessary to achieve a satisfactory solubility causes undesirable degradation of the material.

TATB and LLM-105 are also soluble in the super acids such as 96% sulfuric acid or trifluoromethanesulfonic acid at the >10% level. However, these are undesirable solvents for use in the laboratory.

The insolubility of TATB and LLM-105 has precluded attempts to recrystallize TATB or LLM-105 in large quantities in the past because of the requirement for either corrosive solvents or large amounts of solvent and high temperatures. Therefore formulation chemists have conventionally used only TATB or LLM-105 as supplied by the manufacturer, which may not have been optimal with respect to crystal morphology, amount of crystal defects and particle size distribution.

SUMMARY

A method in one embodiment includes contacting a strongly hydrogen bonded organic material with an ionic liquid having a fluoride anion for solubilizing the strongly hydrogen bonded organic material; and maintaining the ionic liquid at a temperature of about 90° C. or less during the contacting.

A method in another embodiment includes contacting a strongly hydrogen bonded organic material with an ionic liquid having an acetate or formate anion for solubilizing the strongly hydrogen bonded organic material; and maintaining the ionic liquid at a temperature of less than about 90° C. during the contacting.

A method for purifying a strongly hydrogen bonded organic material according to one another embodiment includes dissolving a strongly hydrogen bonded organic material, selected from a group consisting of 1,3,5-triamino-2,4,6-trinitrobenzene and 2,6-diamino-3,5-dinitropyrazine-1-oxide, in a solution comprising an ionic liquid, the ionic liquid having an anion selected from a group consisting of a fluoride anion, an acetate anion, and a formate anion; maintaining the solution at a temperature of about 70° C. or less during the contacting; and recrystallizing the strongly hydrogen bonded organic material.

Other aspects and embodiments of the present invention will become apparent from the following detailed description, which, when taken in conjunction with the drawings, illustrate by way of example the principles of the invention.

DETAILED DESCRIPTION

Figure 1:
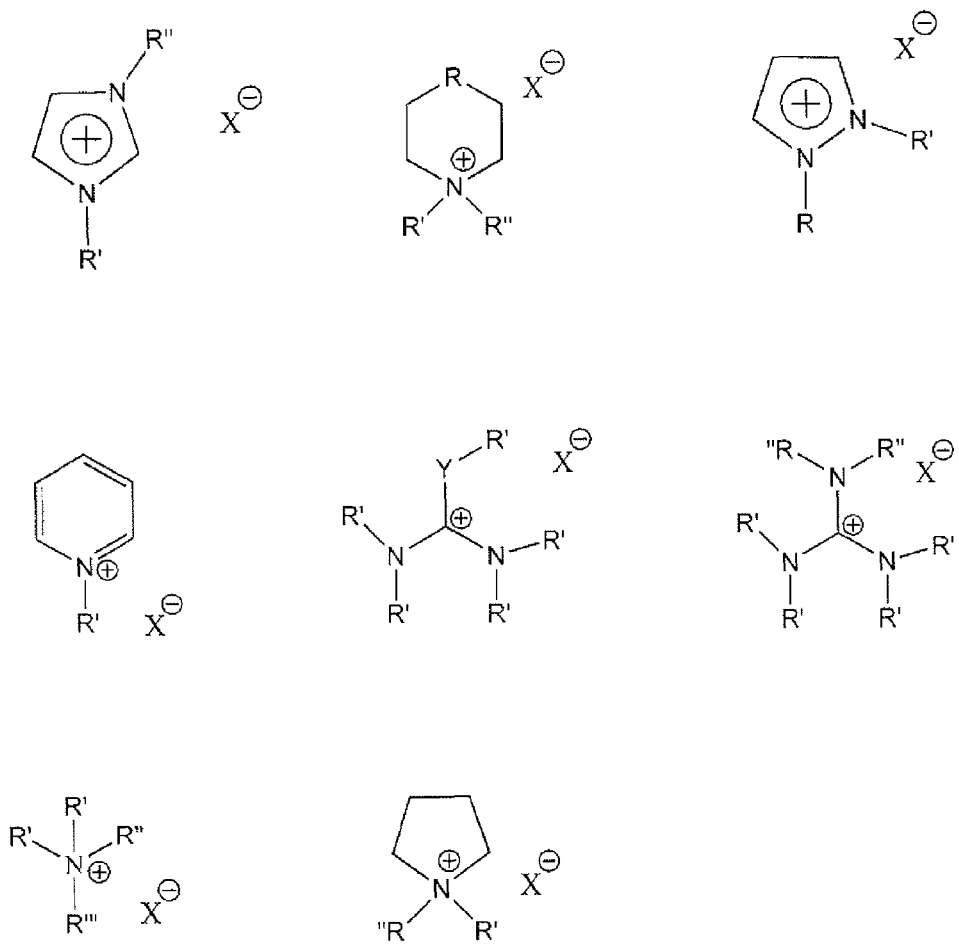
FIG. 1 illustrates several structures of ionic liquids, or their precursors, that may be used in various embodiments

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description, according to some embodiments, describes the use of ionic liquids (ILs) containing the fluoride anion as highly effective solvents for strongly hydrogen bonded materials such as TATB and LLM-105.

Other embodiments relate to the recrystallization of strongly hydrogen bonded organic materials such as TATB and LLM-105 from ILs to yield a strongly hydrogen bonded organic material with improved crystal morphology and purity. For example, TATB and LLM-105 are insensitive energetic compounds used in both conventional and nuclear weapon applications. The recrystallization and purification of these compounds using IL's may lead to improved crystal morphology of the pure compounds. It may also lead to improved safety characteristics and mechanical properties of formulations of the recrystallized compounds with an appropriate polymeric binder.

Further embodiments relate to the synthesis and characterization of several new fluoride-containing ILs and methods used to measure the solubility of TATB, LLM-105 and other substrates in both commercially available and newly synthesized ILs.

Yet further embodiments include the use of a mixed solvent system, where a solvent is added to acetate- and formate-containing ILs as a co-solvent to not only solubilize highly electrophilic substrates (e.g. TATB) but also function as a versatile solvent for the vicarious nucleophilic substitution of hydrogen on electrophilic substrates such as 2,4,6-trinitroaniline (picramide).

Still further embodiments relate to the use of acetate- and formate-containing ILs as effective solvents for strongly hydrogen bonded organic materials such as TATB and LLM-105.

Accordingly, a method in one general approach includes contacting a strongly hydrogen bonded organic material with an IL having a fluoride anion for solubilizing the strongly hydrogen bonded organic material, and maintaining the IL at a temperature of about 90° C. (e.g., 90±3° C.) or less during the contacting.

A method in another general approach includes contacting a strongly hydrogen bonded organic material with an IL having an acetate or formate anion for solubilizing the strongly hydrogen bonded organic material, and maintaining the IL at a temperature of less than about 90° C. during the contacting.

A method for purifying a strongly hydrogen bonded organic material according to another general embodiment includes dissolving a strongly hydrogen bonded organic material, selected from a group consisting of TATB and LLM-105, in a solution comprising an IL, the IL having an anion selected from a group consisting of a fluoride anion, an acetate anion, and a formate anion. The solution is maintained at a temperature of about 70° C. (e.g., 70±3° C.) or less during the contacting. The strongly hydrogen bonded organic material is recrystallized.

Strongly Hydrogen Bonded Organic Materials

Strongly hydrogen bonded organic materials may generally be considered those that have a high cohesive energy density (CED). CED is often expressed in its square-root form, known as the solubility parameter $\delta$. For cellulose, a variety of measurements, including mechanical and surface free energy measurements suggest a value of $\delta \sim 25$ $(MPa)^{1/2}$ [R. J. Roberts and R. C. Rowe, Int. J. Pharm. 99, 157 (1993)]. For TATB, the heat of sublimation (i.e. cohesive energy per molecule) is ~40.2 kcal/mol [J. M. Rosen and C. Dickinson, J. Chem. Eng. Data 14, 120 (1969)]. This, coupled with a molar volume of 221.2 $Å^3$ in the crystal phase [H. H. Cady, and A. C. Larson, Acta Crystallogr., Part 3, 18, 485 (1965)] yields a value of $\delta \sim 35.5$ $(MPa)^{1/2}$. In other words, the CED ($=\delta^2$) of TATB is approximately 2 times that of cellulose, and explains why the former is more difficult to dissolve than the latter. Strongly hydrogen bonded materials may generally be considered those material that have a solubility in water at atmospheric pressure and ambient temperature that is the same or greater than that of cellulose having a chain length of at least 800.]

Illustrative strongly hydrogen bonded organic materials include TATB, LLM-105, cellulose (chain length $\geqq 800$), various peptides, various polysaccharides, etc.

Ionic Liquids (ILs)

Preferred ILs are non-coordinating organic salts that generally have extremely low volatility, are non-flammable, and have a high thermal stability. In particularly preferred approaches, the ILs are "green" solvents that have low vapor pressures and may be recyclable.

ILs used in the various methods disclosed herein, or their precursors, generally include large organic cations (e.g., 1,3-dialkylimidazolium) and may have a variety of different counter-anions. The identities of both the cation and anion may be modified to fine-tune the properties of the resulting IL for desired solvent properties.

Preferred ILs melt at or below about 150° C. ILs that are liquid at ambient temperature are referred to as room temperature ionic liquids (RTILs) and may be most practical for commercial use. Some of the common anions of RTILs include $BF_4^-$, $AlCl_4^-$, $PF_6^-$, $SbF_6^-$, and $-N(OCOCF_3)^-$.

In one approach, ILs containing the fluoride counter-anion are used as effective "green" solvents for strongly hydrogen bonded organic materials, including TATB and LLM-105. Without wishing to be bound by any particular theory, it is believed that ILs containing the fluoride anion are very effective at solubilizing TATB primarily due to the strong hydrogen bonding between the fluoride anion and the $-NH_2$ groups of TATB.

Preferred ILs include imidazoliums, pyrrolidiniums, pyrazoliniums, morpholiniums, 1,2,4-triazolinium, 1,2,3,4-tetrazolinium, uronium, guanidinium etc. Illustrative ILs comprise cations selected from a group consisting of 3-alkyl-1-methylimidazolium, 1-alkylpyridinium, N-methyl-N-alkylpyrrolidinium, 1-methyl-4-alkyl-1,2-triazolinium, 1-methyl-(2, 3 or 4)-alkyltetrazolinium and tetraalkylammonium.

FIG. 1 illustrates several structures of ILs, or their precursors, that may be used in various embodiments. Additional ILs are listed in provisional U.S. application Ser. No. 60/927,845 filed on May 3, 2007, which has been incorporated by reference.

The alkyl groups in the cations of the ILs, in some approaches, may include any short chain alkyl group, e.g., C1-C20. Further, the alkyl groups on a given cation may be the same in some approaches, but are preferably different. For imidazolium cations, the alkyl groups coupled to the nitrogen atoms are preferably different, thereby forming an asymmetric imidazolium cation.

One particularly preferred IL is 3-ethyl-1-methylimidazolium fluoride (EMImF). Other imidazolium ILs include 1,3-dimethylimidazolium fluoride, 3-ethyl-1,2-dimethylimidazolium fluoride, and 3-butyl-1,2-dimethylimidazolium fluoride.

As noted below, experimentally it was found that fluoride-containing ILs are indeed very effective solvents for TATB and LLM-105, offering as much as a 100-fold improvement in solubility over conventional solvents such as dimethylsulfoxide (DMSO). For example, experimental results that showed that 3-ethyl-1-methylimidazolium fluoride dissolved 9.3% w/v of TATB at 90° C. At this temperature (90° C.) DMSO dissolves only 0.9% w/v of TATB.

Figure 2:
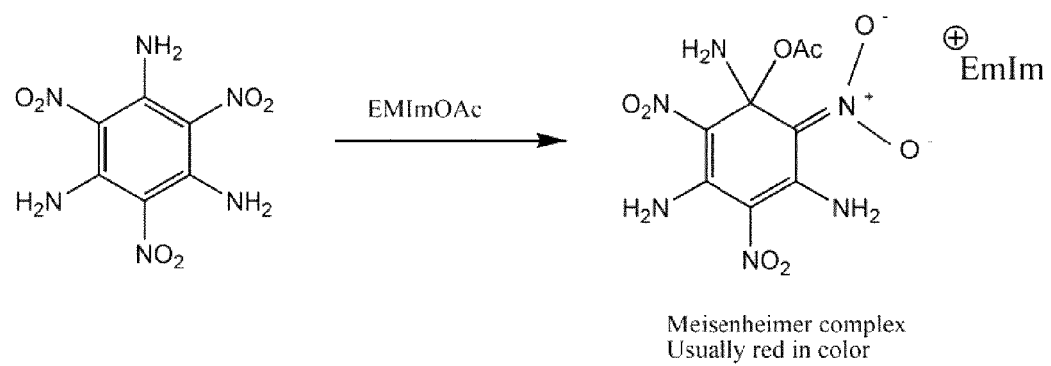
FIG. 2 illustrates formation of a Meisenheimer Complex from TATB and 3-ethyl-1-methylimidazolium acetate.

ILs containing the acetate or formate anion are also effective solvents for strongly hydrogen bonded organic materials such as TATB and LLM-105 when used alone, or in combination with a cosolvent. One particularly preferred acetate-containing IL is 3-ethyl-1-methylimidazolium acetate (EMImOAc). EMImOAc is commercially available. As shown in FIG. 2, mixing TATB with EMImOAc results in a Meisenheimer complex of TATB with the IL. The mixture is usually red in color.

As alluded to in the previous paragraph, cosolvents may be used with the ILs in some approaches. In one approach, a cosolvent such as DMSO is used to reduce the viscosity of the IL. In another approach, the cosolvent may be added to reduce cost.

Illustrative cosolvents include DMSO, dimethylformamide, methylpyrolidinone, sulfolane, and the like.

The cosolvent may be present from >0 to about 90% by weight, more preferably between about 50% and about 85% by weight, and more preferably between about 75% and about 85% by weight. In one illustrative approach, the solvent solution includes about 10-30% EMImOAc and about 70-90% DMSO.

Synthesis of Ionic Liquids

Fluoride-containing ILs may be prepared by many methods. Preferred methods include metathesis and ion exchange, though any suitable method may be used.

ILs having a fluoride anion may be formed by metathesis of a corresponding halogen-containing IL with a fluoride. Metathesis is a bimolecular process involving the exchange of bonds between the two reacting chemical species, which results in the creation of products with similar or identical bonding affiliations. Those skilled in the art will appreciate the many possible methods of metathesis that may be employed to provide a fluoride-containing IL. In one illustrative approach, fluoride-containing ILs may be prepared by metathesis of the corresponding chloride- or bromide-containing IL with a fluoride source, e.g., AgF, in a solvent such as water, removal of the precipitated AgCl or AgBr, followed by removal of the solvent under heat and vacuum.

Ion exchange is an exchange of ions between two electrolytes or between an electrolyte solution and a complex. Ion exchange processes may incorporate an ion exchange resin, which is a matrix (or support structure) typically in the form of small (e.g., 1-2 mm diameter) beads, usually white or yellowish, fabricated from an organic polymer substrate. The material has highly developed structure of pores on the surface of which are sites with easily trapped and released ions. The trapping of ions takes place with simultaneous releasing of other ions; thus the process is called ion exchange. There are multiple different types of ion exchange resin which are fabricated to selectively prefer one or several different types of ions. Accordingly, ILs having a fluoride anion may be formed by treatment of a corresponding halogen-containing IL with a fluoride anion exchange resin. Those skilled in the art will appreciate the many possible methods of ion exchange that may be employed to provide a fluoride-containing IL. In one illustrative approach, fluoride-containing ILs may be prepared by treatment of the corresponding chloride- or bromide-containing IL with a fluoride anion exchange resin (e.g., 5-10 fold molar excess of resin) followed by removal of the solvent under heat and vacuum.

Some ILs are isolated as either white to brown solids or relatively viscous tan to red oils. Crystalline ILs may be purified by re-precipitation of the ILs. In one approach, fluoride-containing ILs may be purified by re-precipitation of the ILs from an acetonitrile/ethanol (MeOH)/ethyl acetate (EtOAc) mixture.

Methods of Solubilizing Strongly Hydrogen Bonded Organic Materials

A method for solubilizing a strongly hydrogen bonded organic material such as TATB and LLM-105 in one general approach includes contacting the strongly hydrogen bonded organic material with an IL having a fluoride anion for solubilizing the strongly hydrogen bonded organic material. The IL is maintained at a temperature of about 90° C. (e.g., 90±3° C.) or less during the contacting.

Preferably, the IL at a temperature of about 50° C. (e.g., 50±3° C.) or less during the contacting. This minimizes thermal degradation of the strongly hydrogen bonded organic material.

One particularly preferred IL is EMImF, though other ILs may be used.

A method in another general approach includes contacting a strongly hydrogen bonded organic material with an IL having an acetate or formate anion for solubilizing the strongly hydrogen bonded organic material, and maintaining the IL at a temperature of less than about 90° C., more preferably about 50° C. or less, during the contacting.

As noted above, a cosolvent such as DMSO may be mixed with the IL, the strongly hydrogen bonded organic material being contacted with both the cosolvent and the strongly hydrogen bonded organic material.

Recrystallization of Strongly Hydrogen Bonded Organic Materials

As noted above, the recrystallization of strongly hydrogen bonded organic materials such as TATB and LLM-105 may improve the crystal morphology and purity of the material. For example, the recrystallization and purification of TATB and LLM-105 using IL's may lead to improved crystal morphology of the substantially pure compounds. It may also lead to improved safety characteristics and mechanical properties of formulations of the recrystallized compounds with an appropriate polymeric binder.

A method for purifying a strongly hydrogen bonded organic material according to one general embodiment includes dissolving a strongly hydrogen bonded organic material in a solution comprising an IL, as noted above. The solution is maintained at a temperature of about 70° C. (e.g., 70±3° C.) or less, preferably about 50° C. or less, during the contacting. Then the strongly hydrogen bonded organic material is recrystallized.

Various approaches may be used to recrystallize the strongly hydrogen bonded organic material. In one approach, the solution is cooled. Cooling reduces the solubility of the solution, thereby inducing precipitation of the material from the solution. Also, the rate of the cooling may be used to adjust the particle size of the material. In general, the faster the cooling, the smaller the particle size.

In another approach, the recrystallizing includes contacting the dissolved strongly hydrogen bonded organic material with an amount of a counter solvent that is effective to induce precipitation of the strongly hydrogen bonded organic material. The counter solvent may be a material that has a hydrogen bonding character or can donate a proton through acidity. Illustrative counter solvents include water, acetic acid, alcohols, organic acids, etc. The rate of addition of the counter solvent may be used to provide a measure of control over the particle size. In general, the slower the addition of the counter solvent, the larger the particle size of the material.

Those skilled in the art will appreciate that other approaches to recrystallizing the strongly hydrogen bonded organic material may be employed.

After recrystallizing, the materials may be washed. For example, the crystals may be washed in water, methanol, ethanol, isopropanol, ethyl acetate, etc.

Atomic Force Microscopy (AFM) may be used to examine crystal growth, dissolution, solubility and morphology.

Experiments with TATB have shown that the purity of the recrystallized strongly hydrogen bonded organic material is higher than a purity of the strongly hydrogen bonded organic material before being dissolved in the solution.

The fluoride-containing ILs are also effective at the recrystallization of TATB producing in some cases spherical crystals or crystals with a low aspect ratio. This improved TATB may lead to new formulations with enhanced insensitivity and fewer defects and reduced ratchet growth.

The resulting strongly hydrogen bonded organic material may be used in any suitable application. For example, TATB and LLM-105 may be used as energetic compounds in both conventional and nuclear weapon applications.

Experimental Examples

Example 1

The solubility tests of Examples 1 and 2 were performed using an optical microscope equipped with a temperature controlled sample holder under crossed polarized light. Crystal solubilities were determined by monitoring the disappearance of their birefringence at various temperatures.

TATB was added to substantially pure 3-ethyl-1-methylimidazolium fluoride at 90° C. About 9.3% w/v of TATB became dissolved in the 1-ethyl-3-methylimidazolium.

Example 2

In a comparative example performed under substantially the same conditions as in Example 1, TATB was dissolved in DMSO at 90° C. It was found that DMSO dissolves only about 0.9% w/v of TATB at that temperature.

Example 3

An excess of TATB was added to substantially pure 3-ethyl-1-methylimidazolium fluoride maintained at 90° C. in a constant temperature oil bath. Any undissolved TATB was allowed to settle. An aliquot was removed and the TATB was precipitated with an excess of water. The recovered material was collected by suction filtration, washed with MeOH and the weight of TATB was noted. The results were consistent with the findings in Example 1.

Example 4

The solubility tests of Examples 4, 5 and 6 were performed using an optical microscope equipped with a temperature controlled sample holder under crossed polarized light. Crystal solubilities were determined by monitoring the disappearance of their birefringence at various temperatures.

TATB was added to 3-ethyl-1-methylimidazolium acetate at 70° C. Approximately 3.2% w/v of TATB was dissolved in the 3-ethyl-1-methylimidazolium acetate at that temperature.

Example 5

TATB was added to 3-ethyl-1-methylimidazolium acetate at 90° C. Approximately 6.0% w/v of TATB was dissolved in the 3-ethyl-1-methylimidazolium acetate at that temperature.

Example 6

TATB was added to an 80:20 (w/w) mixture of dimethylsulfoxide and 3-ethyl-1-methylimidazolium acetate at room temperature (e.g., 22° C.). Approximately 1.5% w/v of TATB was dissolved. This is a significant increase when compared to pure DMSO which dissolves only about 0.2% w/v of TATB at room temperature.

Without wishing to be bound by any theory, it is postulated that the IL forms a Meisenheimer complex with the TATB, thus increasing its solubility. The DMSO enhances the basicity of the IL by preferentially solubilizing the organic cation thus producing a more basic, "naked" acetate or formate anion.

Example 7

Fabrication of 3-Ethyl-1,2-dimethylimidazolium Fluoride (EDMImF)

3-Ethyl-1,2-dimethylimidazolium chloride (25 g, 0.16 mol) was dissolved with stirring in water (100 mL). To this was added dropwise a solution of AgF (19.8 g, 0.16 mol) in water (50 mL). The AgCl product precipitated immediately upon addition. The mixture was stirred 1 h at room temperature and the AgCl was removed by suction filtration (21.2 g, 0.16 mol). The solution was allowed to stand overnight to ensure no additional AgCl or Ag metal precipitated. The solution was filtered by gravity and the solvent was removed under vacuum at 45° C. to yield beige crystals. The product was dissolved in a mixture of acetonitrile (AcN) (75 mL) and methanol (MeOH) (15 mL), dried over molecular sieves and the solvent was removed to yield a sticky crystalline solid. Ethyl acetate (EtOAc) was added and the crystals were collected by suction filtration. Drying at 50° C. under high vacuum yielded light beige crystals; m.p. 135° C.

Example 8

Fabrication of 3-Ethyl-1-methylimidazolium fluoride (EMImF)

The same general procedure as used in Example 7 was performed, except for use of 3-ethyl-1-methylimidazolium chloride (25.8 g, 0.18 mol) as the substrate and 25.4 g (0.2 mol) of AgF. This yielded a tan viscous liquid that slowly crystallizes upon sitting.

Example 9

Fabrication of 3-Allyl-1-methylimidazolium Fluoride (AlMImF)

The same general procedure as used in Example 7 was performed, except for use of 3-allyl-1-methylimidazolium chloride (25 g). Removal of the solvent after treatment with molecular sieves yielded a brown cloudy oil (27 g).

Example 10

Fabrication of 3-Butyl-1-methylimidazolium fluoride (BuMImF)

The same general procedure as used in Example 7 was performed, except for use of 3-butyl-1-methylimidazolium chloride (25 g). Removal of the solvent yielded 24 g of a light tan oil.

Example 11

Fabrication of 3-(Methoxymethyl)-1-methylimidazolium fluoride (MOMImF)

The same general procedure as used in Example 11 was performed, except for use of 3-(Methoxymethyl)-1-methylimidazolium chloride (25 g). Removal of the solvent yielded 24 g of a yellow oil. Upon sitting a small amount of crystals formed which were collected by filtration under argon (3.3 g).

Example 12

Fabrication of 3-(Methoxymethyl)-1-methylimidazolium chloride

Into a 500 mL round-bottomed flask equipped with a stir bar, Argon inlet and addition funnel was dissolved 1-methylimidazole (25 g, 0.31 mol) in trichloroethylene (100 mL). With stirring chloromethyl methyl ether (35 g, 0.43 mol) was added slowly dropwise over a 0.5 h period. The mixture warmed and a turbid, two-layer mixture formed upon addition. The mixture was refluxed 2 h, cooled and poured into a separatory funnel. The organic layer was separated, filtered and the solvent was removed under vacuum at 45° C. to yield a tan-beige viscous liquid (52 g).

Example 13

Sample Prep of Fluoride-Containing IL by Ion Exchange 230 grams of ammonium fluoride was dissolved in 1500 mL of water. To this solution 500 grams of DOWEX 1×4-50 ion exchange resin (chloride form) was added and the mixture is stirred for 2 hours. The resulting fluoride-exchanged resin was washed with 3000 mL of de-ionized and distilled water. The resulting mixture was filtered and washed with another 2000 mL of de-ionized and distilled water. This fluoride-exchanged resin was mixed with anhydrous methanol and the resulting slurry was packed in a wide bore (5 cm diameter; 35 cm length) chromatography column fitted with a frit. The packed column was flushed with methanol.

0.91 grams of 3-ethyl-1-methyl imidazolium chloride (Fluka) IL was dissolved in 25 mL of anhydrous methanol to give a clear green solution. This solution was added to the column and allowed to flow through with added methanol to rinse the eluent. Approximately 500 mL of raw eluent was recovered. This aliquot was roto-evaporated at 65° C. to give 14 grams of an amber liquid. This aliquot was dried on a vacuum line at 70° C. for 2 h and 80° C. for 1 h. After drying the material had turned to a highly viscous red/orange liquid.

Example 14

Recrystallization of TATB from 20:80 3-ethyl-1-methylimidazolium acetate/DMSO solution using a counter-solvent Into a 4-necked 100 mL round-bottomed flask equipped with an overhead stirrer, drying tube, thermocouple and septum inlet was placed 20 mL of a 20:80 3-ethyl-1-methylimidazolium acetate/DMSO solution. To this was added TATB (0.5 g) and the mixture was stirred and heated slightly until all the TATB dissolved and a red-orange solution was formed. The sample was heated to a desired temperature using a J-KEM controller. The mixture was stirred slowly as a solution of boric acid (4 g) in dry DMSO (40 mL) was added via a syringe and long needle connected to a syringe pump set at 2 mL/hr. The resulting TATB was collected by suction filtration, washed with water (25 mL) and MeOH (10 mL) to yield 0.44 g of a yellow microcrystalline solid. The purity (99%) of the TATB was determined by HPLC analysis.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method, comprising:
   contacting 1,3,5-triamino-2,4,6-trinitrobenzene with an imidazolium ionic liquid having a fluoride anion; and
   maintaining the imidazolium ionic liquid at a temperature of about 90° C. or less during the contacting.

2. A method, comprising:
   contacting 1,3,5-triamino-2,4,6-trinitrobenzene with an imidazolium ionic liquid having an acetate or formate anion; and
   maintaining the imidazolium ionic liquid at a temperature of less than about 90° C. during the contacting.

3. The method of claim 2, further comprising mixing dimethylsulfoxide with the imidazolium ionic liquid.

4. The method of claim 2, wherein the ionic liquid having the acetate or formate anion is 1-ethyl-3-methylimidazolium acetate.

5. The method of claim 2, wherein the ionic liquid is 1-alkyl-3-methylimidazolium.

6. The method of claim 2, wherein the 1,3,5-triamino-2,4,6-trinitrobenzene becomes solubilized upon contacting the imidazolium ionic liquid, and further comprising recrystallizing the solubilized 1,3,5-triamino-2,4,6-trinitrobenzene.

7. The method of claim 6, wherein a purity of the recrystallized 1,3,5-triamino-2,4,6-trinitrobenzene is higher than a purity of the 1,3,5-triamino-2,4,6-trinitrobenzene before being contacted with the imidazolium ionic liquid.

* * * * *